United States Patent
Kelly et al.

(10) Patent No.: US 7,277,176 B2
(45) Date of Patent: Oct. 2, 2007

(54) EMISSION FILTER X-Y ARRAY

(75) Inventors: Darius Kelly, Alta Loma, CA (US); Sean Gallager, Claremont, CA (US); Jeff Pieri, Pasadena, CA (US); Dave Wick, Menifee, CA (US)

(73) Assignee: UVP, Inc., Upland, CA (US)

( * ) Notice: Subject to any disclaimer, the term of this patent is extended or adjusted under 35 U.S.C. 154(b) by 202 days.

(21) Appl. No.: 11/126,547

(22) Filed: May 10, 2005

(65) Prior Publication Data

US 2006/0256337 A1 Nov. 16, 2006

(51) Int. Cl.
*G01N 21/25* (2006.01)
*G05G 11/00* (2006.01)
*G01J 3/51* (2006.01)

(52) U.S. Cl. .................... 356/419; 356/419; 250/226; 74/490.09

(58) Field of Classification Search ............... 356/419; 348/268, 270; 74/49.09, 89.33
See application file for complete search history.

(56) References Cited

U.S. PATENT DOCUMENTS

| | | | |
|---|---|---|---|
| 2,617,875 A * | 11/1952 | De Forest | 348/270 |
| 2,721,893 A * | 10/1955 | Vanderhooft | 348/270 |
| 3,495,519 A * | 2/1970 | Bluitt et al. | 106/137 |
| 3,936,186 A | 2/1976 | Boland et al. | |
| 4,141,653 A * | 2/1979 | Arnold | 356/419 |
| 4,777,133 A * | 10/1988 | Picciolo et al. | 435/7.22 |
| 4,907,280 A * | 3/1990 | Barney et al. | 382/323 |
| 4,995,277 A * | 2/1991 | Yanagisawa | 74/490.09 |
| 5,175,437 A | 12/1992 | Waluszko | |
| 5,231,537 A * | 7/1993 | Hama | 359/889 |
| 5,288,647 A | 2/1994 | Zimlich, Jr. et al. | |
| 5,311,791 A * | 5/1994 | Yanagisawa | 74/490.09 |
| 5,736,744 A | 4/1998 | Johannsen et al. | |
| 5,881,466 A * | 3/1999 | Yamaguchi et al. | 33/1 M |
| 5,951,838 A | 9/1999 | Heffelfinger et al. | |
| 5,969,868 A * | 10/1999 | Bornhorst et al. | 359/589 |
| 6,327,929 B1 * | 12/2001 | Yanagisawa | 74/490.09 |
| 2003/0178555 A1 * | 9/2003 | Fang | 250/226 |
| 2004/0007675 A1 * | 1/2004 | Gillispie et al. | 250/458.1 |
| 2005/0036139 A1 * | 2/2005 | Johnson | 356/246 |
| 2005/0105080 A1 * | 5/2005 | Landinger | 356/73 |

* cited by examiner

*Primary Examiner*—Gregory J. Toatley, Jr.
*Assistant Examiner*—Bryan J Giglio
(74) *Attorney, Agent, or Firm*—James E. Brunton, Esq.

(57) ABSTRACT

An imaging system for obtaining images of a specimen that includes a novel filtering system for filtering radiation emitted from the specimen. The imaging system includes a camera and a novel filter grid that is controllably movable relative to the camera in a manner to move a selected emission filter of a plurality of emission filters carried by the grid into position between the camera and the specimen. The filter carrying grid of the system resides in a plane having X and Y coordinates and the system includes a novel positioning mechanism for controllably moving the filter carrying grid along the X and Y coordinates of the plane in a manner to position a selected one of the emission filters carried by the grid into position between the camera and the specimen.

15 Claims, 7 Drawing Sheets

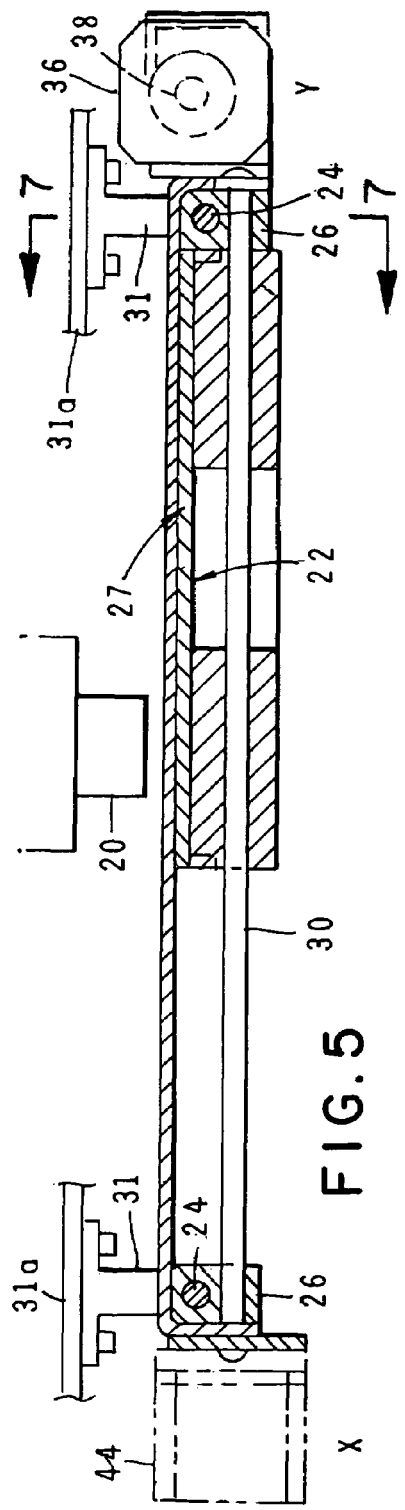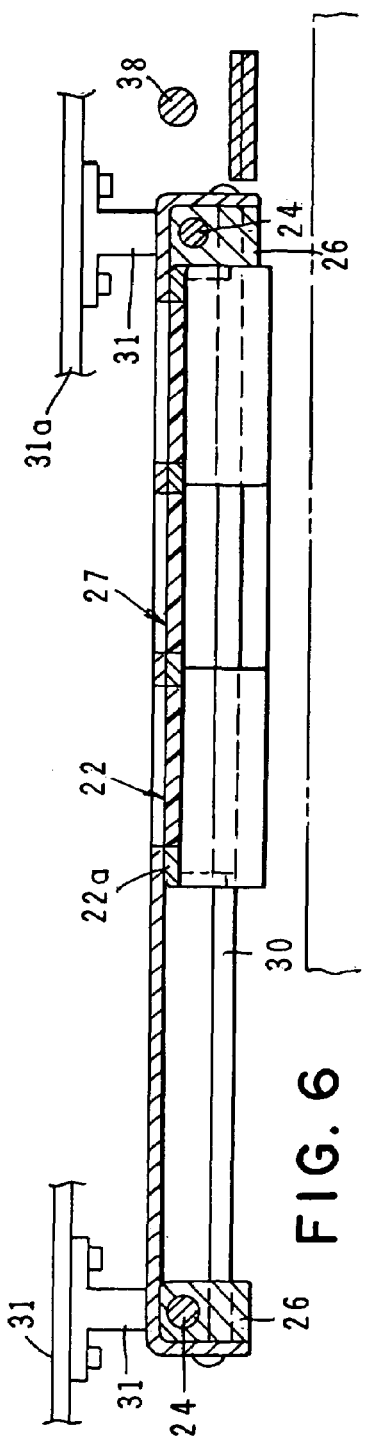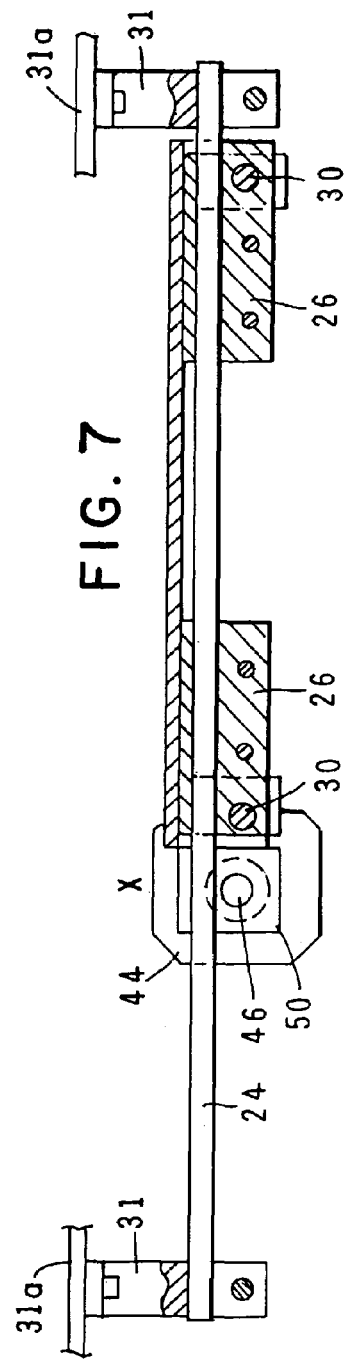

EMISSION FILTER X-Y ARRAY

BACKGROUND OF THE INVENTION

1. Field of the Invention

The present invention relates generally to imaging systems for obtaining images of a specimen. More particularly, the invention concerns an imaging system which includes a camera and a novel filter grid that is controllably movable relative to the camera in a manner to strategically move a selected emission filter grid, comprising a plurality of emission filters, into position between the camera and the specimen.

2. Discussion of the Prior Art

Imaging systems of many kinds are widely used in the prior art to obtain images of various types of objects. Typically the imaging system includes a camera and oftentimes one or more special filters that are positioned between the camera lens and the object to filter the light reaching the camera.

The apparatus of the present invention is particularly useful in the field of fluorescence imaging, but is not limited to this application. Fluorescence imaging is typically performed by illuminating a specimen in a manner to excite fluorescing molecules in the specimen, and then, using a suitable camera, capturing an image of the specimen as it fluoresces.

As a general rule, intensified or cooled charge-coupled device (CCD) cameras are used to detect the fluorescence of low intensity light radiating from the sample. The image capture, of course, requires that the specimen be illuminated with a suitable illumination source, while the minute amounts of fluoresced energy from the "excited" sample are detected using the CCD camera. In carrying out the imaging process, the CCD camera is typically fixed at a single location over a specimen supporting platform and the operator places a specimen in a predetermined position on the specimen supporting platform within the field of view of the overhead camera.

In obtaining the desired image of the specimen, it is generally necessary to position an appropriate emission filter between the specimen and the camera to filter out the excitation light rays and leave substantially only the fluorescent rays emanating from the sample. In the prior art, an emission filter wheel has been used to accomplish the appropriate filtering out of the excitation light rays. This filter wheel is typically housed within the imaging chamber within which the specimen resides and is rotatable in a manner to bring a selected one of the circular shaped emission filters carried by the filter wheel into a position between the specimen and the lens of the camera wheel. Such a construction is provided in an imaging station sold by the Kodak Digital Science Company using the model number 440CF. The filter wheel of this latter system contains filters for different detection methods and includes five standard 58 mm filters positioned in circumferentially spaced apart locations.

As will be discussed in greater detail hereinafter, the apparatus of the present invention constitutes a substantial improvement over the prior art filter wheels and includes a novel X-Y array, or grid, within which nine generally rectangular shaped filters are mounted. In the preferred embodiment of the invention, the grid can be quickly and precisely moved by means of electric motors along both the X- and Y-axes of the grid system in a manner to bring a desired one of the emission filters into position between the specimen and the camera lens.

Prior art imaging systems include, by way of example, the system disclosed in U.S. Pat. No. 5,175,437 issued to Waluszko. More particularly, this patent describes an apparatus for irradiating an object such as a specimen of material with ultraviolet radiation at selected long, short or mid-wave length.

U.S. Pat. No. 5,736,744 issued to Johannsen, et al. discloses a wavelength-shifting filter having two sheets of material adjacent and parallel with a spacer there between and with the sheets held in a frame. A phosphor coating is located on the inner side of one of the sheets. A transilluminator is associated with the filter and provides radiation in the UV wavelength. One sheet of the filter transmits the UV wavelength. The other sheet transmits at least a portion of the wavelength that the phosphor coating generates when subjected to the UV radiation of the transilluminator.

In a somewhat similar vein, U.S. Pat. No. 3,936,186 issued to Boland et al., discloses an apparatus for exposing diazo printing plates and the like of the character that are used in the graphic arts field. In like manner, U.S. Pat. No. 5,288,647 issued to Zimlich, Jr. et al., relates to a method by which polynucleotide specimens can be irradiated particularly for the purpose of fixing them to a substrate.

U.S. Pat. No. 5,951,838 issued to Heffelfinger et al., concerns a method and apparatus for achieving uniform illumination of an electrophoresis apparatus. In the Heffelfinger et al., method, uniform illumination is achieved by scanning the light source across the sample gel in a direction perpendicular to the axis of the source. The light source is comprised of one or more light bulbs placed in a light tray. Variations in light intensity near the source end portions is minimized using a variety of techniques including extended light bulbs, filters, reflectors, and diffusers, or supplemental sources.

SUMMARY OF THE INVENTION

It is an object of the present invention to provide an imaging system for obtaining images of a specimen that includes a novel filtering system for filtering radiation emitted from the specimen. More particularly, it is an object of the invention to provide an imaging system which includes a camera and a novel filter grid that is controllably movable relative to the camera in a manner to move a selected emission filter of a plurality of emission filters carried by the grid into position between the camera and the specimen.

Another object of the invention is to provide an imaging system of the aforementioned character in which the filter carrying grid resides in a plane P having X and Y rectangular coordinates and in which the invention includes a novel positioning system for controllably moving the filter carrying grid along the X and Y coordinates of the plane in a manner to position a selected one of the emission filters carried by the grid into position between the camera and the specimen.

Another object of the invention is to provide an imaging system as described in the preceding paragraphs in which the filter grid carries nine differently colored filters in a side by side relationship.

Another object of the invention is to provide an imaging system as described in the preceding paragraph in which the filter carrying grid can be positioned manually, or alternatively, can be automatically positioned by electric motors that are controlled by pre-programmed software.

Another object of the invention is to provide an imaging system of the character described in which the filter grid of the apparatus can be easily replaced by a filter grid carrying differently colored filters.

Another object of the invention is to provide an imaging system as described in the preceding paragraphs which is of a simple construction and is easy to use with a minimum of instruction.

The foregoing, as well as other objects of the invention can be achieved by the novel imaging system described in the following paragraphs.

BRIEF DESCRIPTION OF THE DRAWINGS

FIG. 5 is a cross-sectional view taken along lines 5-5 of FIG. 4.

FIG. 6 is a cross-sectional view tank along lines 6-6 of FIG. 4.

FIG. 7 is a cross-sectional view taken along lines 7-7 of FIG. 5.

DESCRIPTION OF THE INVENTION

Figure 1:
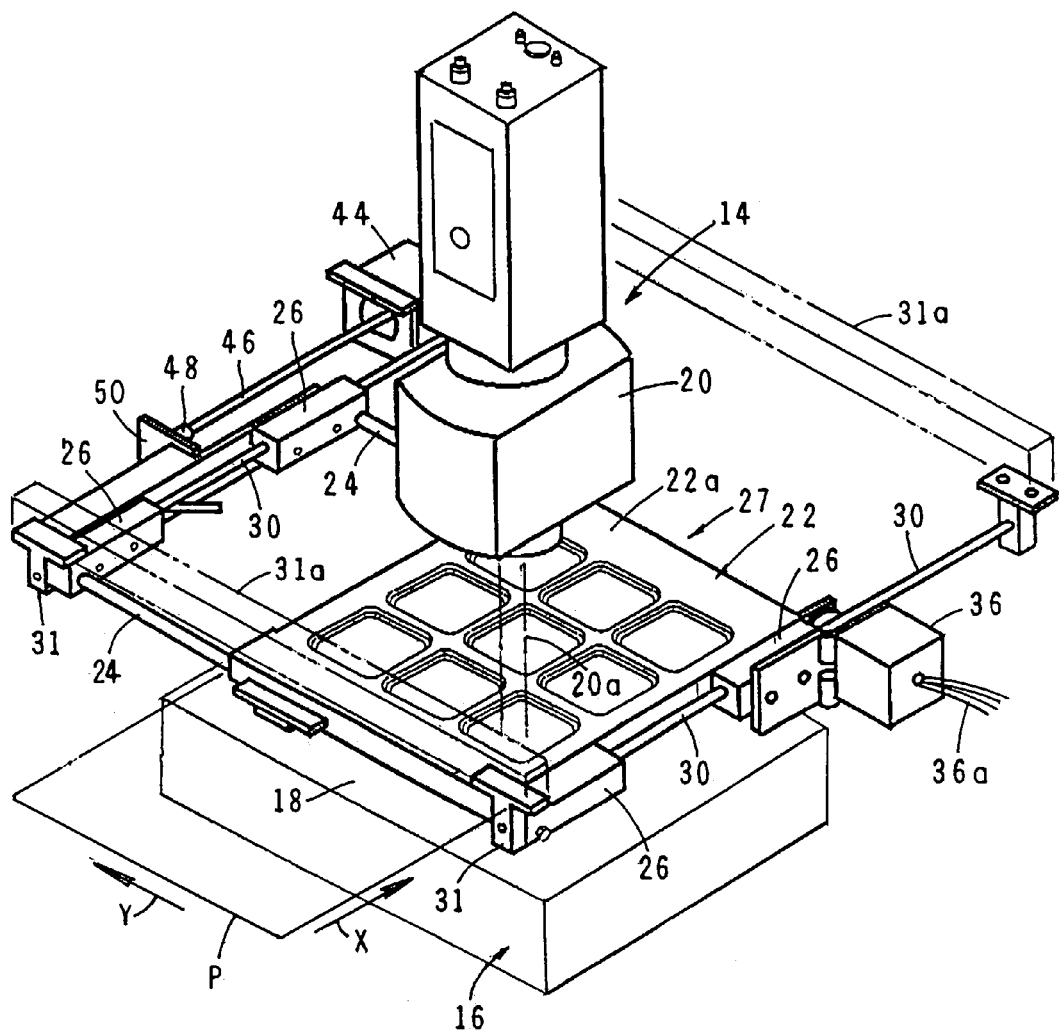
FIG. 1 is a generally perspective view of one form of imaging system of the present invention.

Referring to the drawings and particularly to FIG. 1, one form of the apparatus of the invention for obtaining images of a specimen is there illustrated and generally designated by the numeral 14. In this form of the invention, the apparatus comprises a support 16 having an upper surface 18 for supporting the specimen and a camera 20 superimposed over the support 16. A novel feature of the apparatus of the invention comprises a filter means superimposed over the support for filtering energy emitted from the specimen. As shown in FIG. 1 of the drawings this important filter means here comprises a filter array 22 for supporting a plurality of emission filters in a side-by-side relationship. More particularly, the filter array here comprises nine generally rectangular shaped emission filters that are mounted within a suitable frame 22a. As indicated in FIG. 1, the filter array 22 is disposed within a plane "P" having X- and Y-axes.

Another novel feature of the apparatus of the invention comprises positioning means for positioning the filter array relative to the field of view of camera 20. In the present form of the invention this novel positioning means comprises guide means operably associated with said filter array for guiding travel of the filter array along the X- and Y-coordinates of plane "P" in a manner to position a selected one of the emission filters within the field of view of said camera.

The positioning means also comprises drive means for moving the filter array along the guide means. More particularly, as will be discussed in greater detail hereinafter, the filter array 22 is slidably movable along a first, or filter array guide means in an X direction by the first drive means of the invention and is movable in a Y direction along a second guide means by the second drive means of the invention. In this way a selected one of the emission filters of the filter array can be controllably positioned within the field of view 20a of camera 20.

Figure 2:
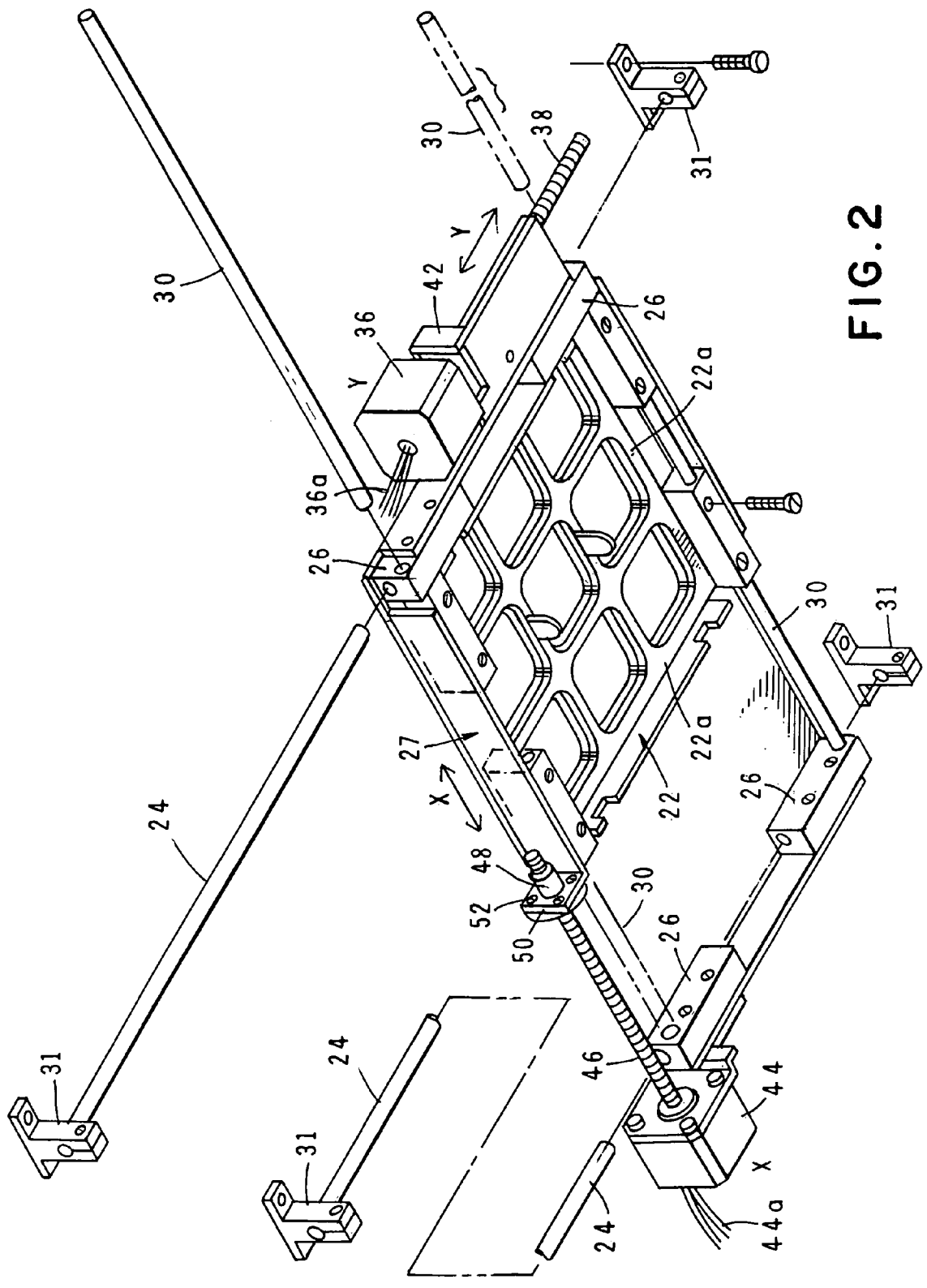
FIG. 2 is a generally perspective exploded bottom view of one form of the filter array of the apparatus of the invention similar to that shown in FIG. 1 and the various mechanisms for moving the filter array along the X and Y coordinates of the plane P within which the filter array resides.

Referring to FIGS. 1 and 2, the filter array guide means portion of the guide means of the invention here comprises a pair of spaced apart first guide rods 24 to which the filter array 22 is slidably connected in a manner shown in FIG. 1. Connected to the extremities of each of the first guide rods 24 is a support bearing 26. The filter array 22, the first guide rods 24 and the support bearings 26 here cooperate to form a filter array assembly that is generally designated in FIG. 1 by the numeral 27.

Operably interconnected with filter array assembly 27 is the second, or filter array assembly guide means portion of the guide means of the invention, which here comprise a pair of spaced apart second guide rods 30. As best seen in FIG. 1, guide rods 30 are slidably receivable within support bearings 26 so as to enable the filter array assembly 27 to be moved along the X-coordinates of plane "P" by the second drive means of the invention, the character of which will presently be described. As indicated in FIG. 1, the ends of spaced apart guide rods 30 are connected to support brackets 31 which are, in turn, connected to a structural support 31a that is shown in FIG. 1 by phantom lines.

Figure 3:
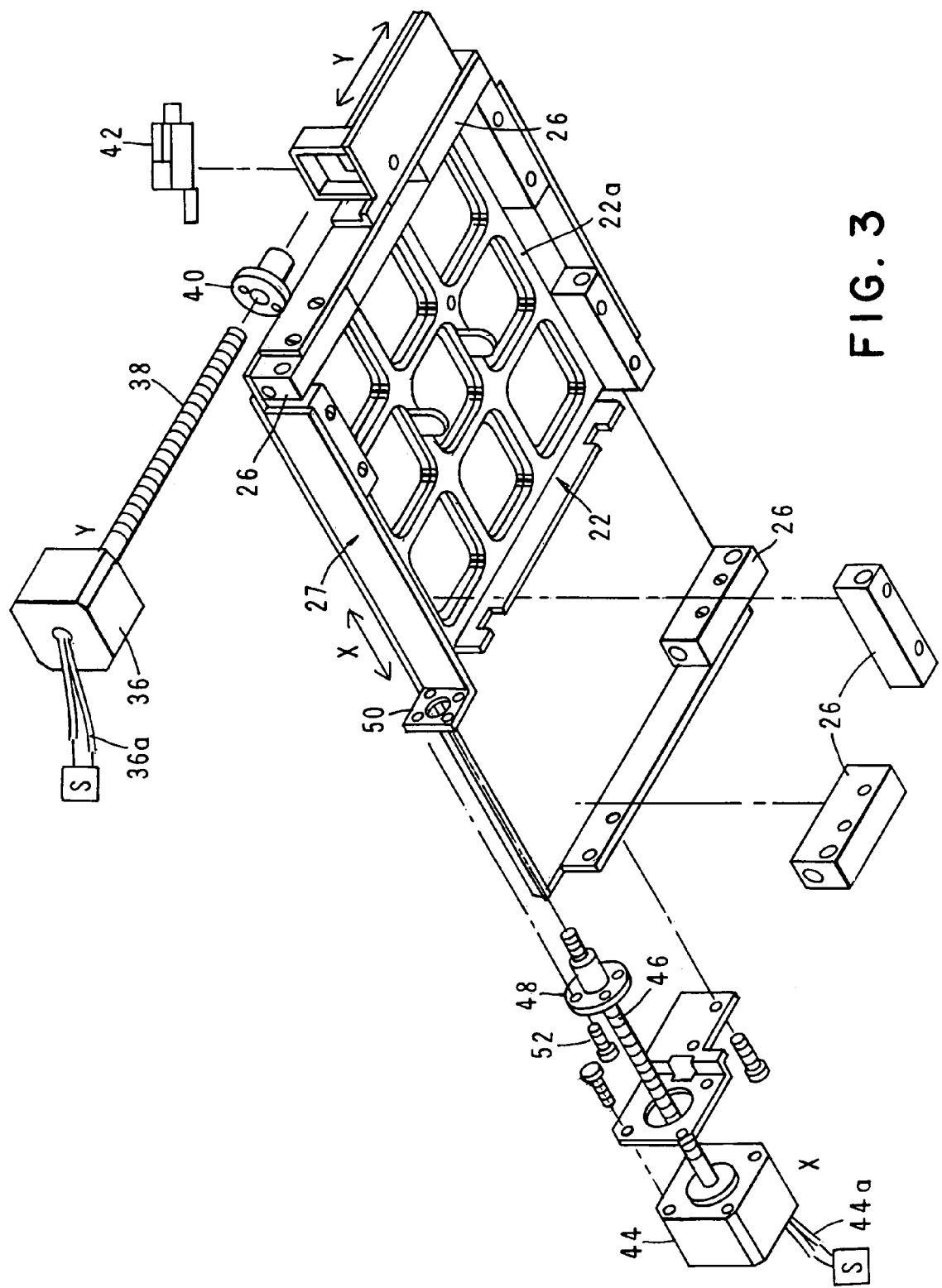
FIG. 3 is a generally perspective exploded bottom view of the filter array of the apparatus of the invention shown in FIG. 2 further illustrating the arrangement and interconnection of the various mechanisms for moving the filter array along the X and Y coordinates of the plane within which the filter array resides.

Turning to FIGS. 1, 2 and 3, the filter array assembly drive means portion of the drive means of the invention for moving the filter assembly 27 in a direction along the Y-coordinates of plane "P" here comprises a readily commercially available electric motor 36 which is connected to a source "S" of electricity by connectors 36a (see FIG. 3). Motor 36 is adapted to rotate a threaded drive screw 38. Drive screw 38 is threadably received within an internally threaded member 40, which is interconnected to a bracket 42 (FIG. 3). Bracket 42 is, in turn, connected to filter assembly 27 so that rotation of drive screw 38 by motor 36 will cause filter assembly 27 to move along guide rods 24 in a direction along the Y-coordinates of plane "P". In similar manner, the filter array drive means portion of the drive means of the invention here comprises a readily commercially available electric motor 44 which is connected to a source "S" of electricity by connectors 44a (see FIG. 3), is adapted to rotate a threaded drive screw 46 that is threadably received within an internally threaded member 48. Threaded member 48 is, in turn, interconnected to a bracket 50 by threaded connectors 52 and bracket 50 is interconnected with the filter assembly 27 in a manner indicated in FIG. 3. With this construction rotation of drive screw 46 by motor 44 will cause filter assembly 27 to move along guide rods 30 in a direction along the X-coordinates of plane "P".

Figure 4:
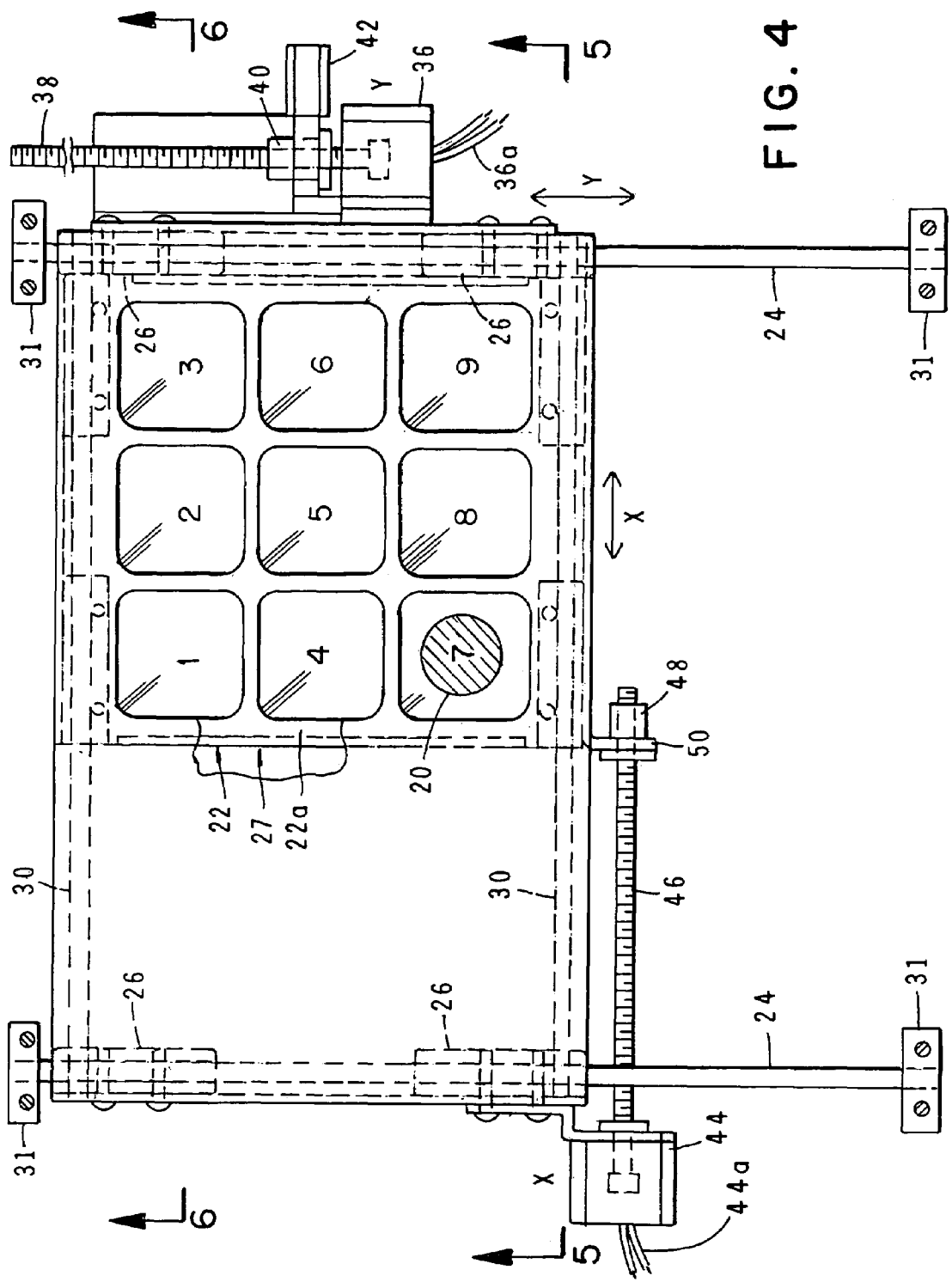
FIG. 4 is a top plan view of the filter array of the apparatus of the invention showing the mechanisms for moving the filter array as they appear in an assembled configuration.
Figure 8:
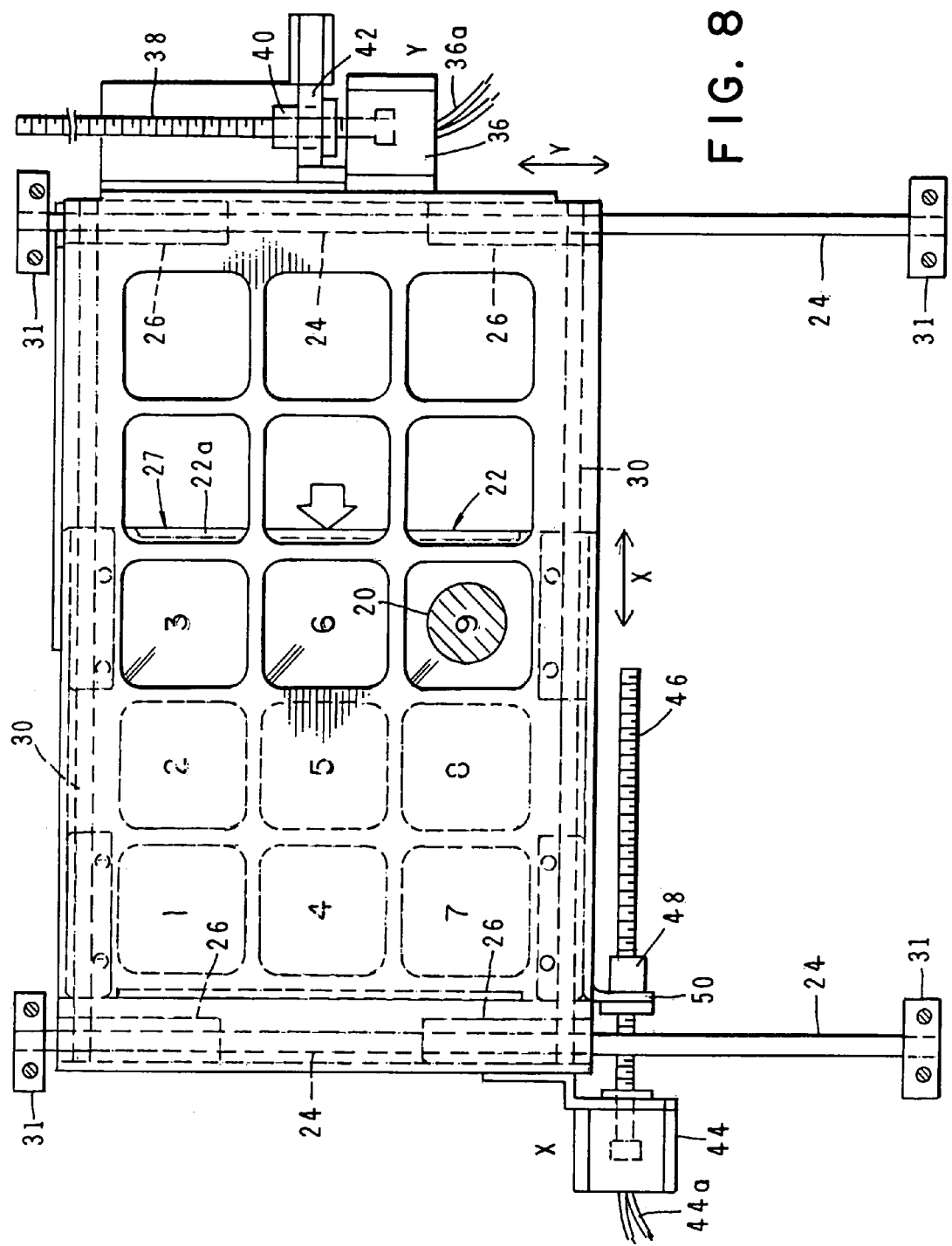
FIG. 8 is a top plan view similar to FIG. 4 but illustrating movement of the filter array along the X-coordinates.
Figure 9:
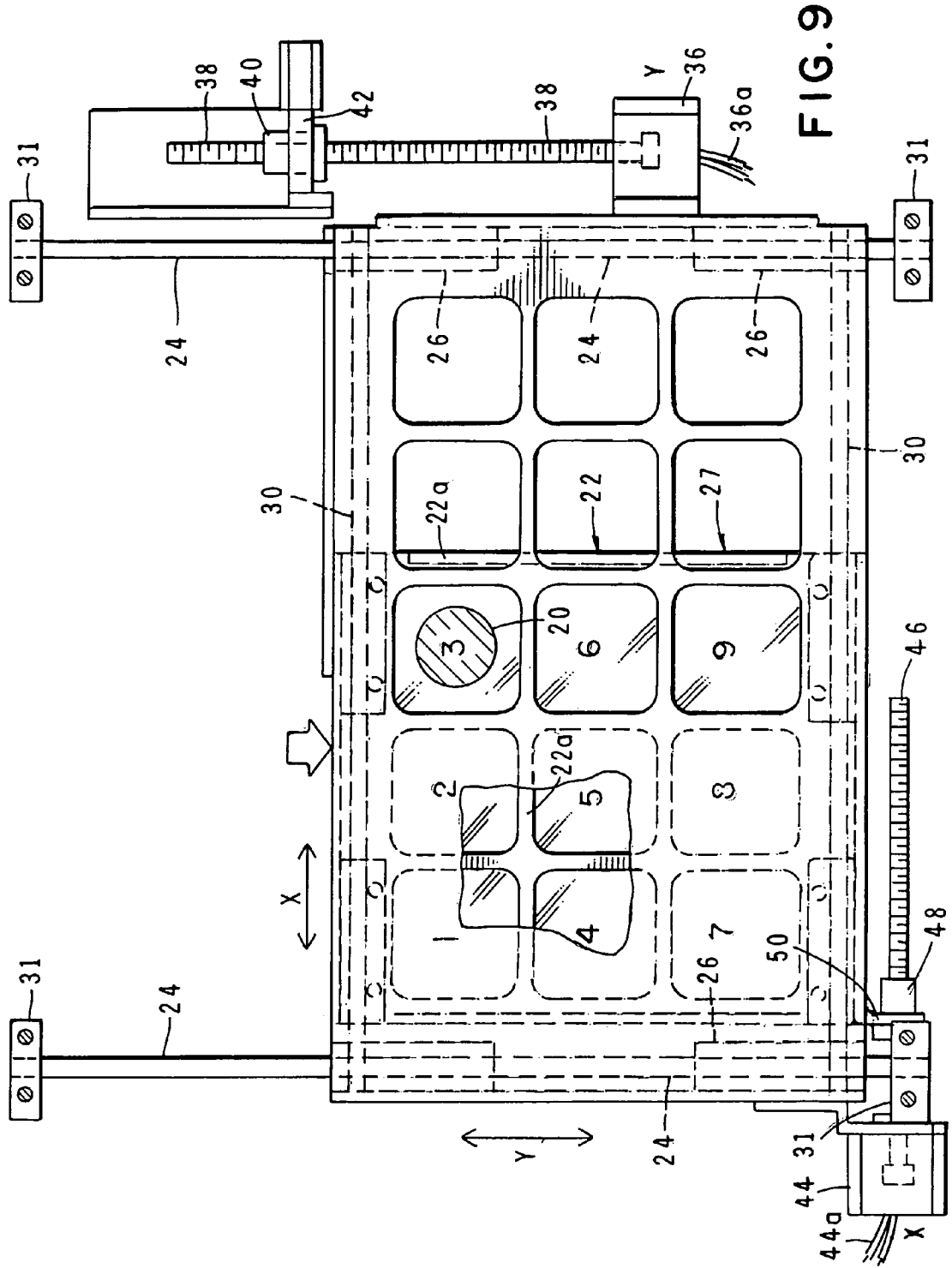
FIG. 9 is a top plan view similar to FIG. 4, but illustrating movement of the sewer array along the Y-coordinates.

Referring next to FIGS. 4 through 7, when the apparatus is fully assembled and the filter assembly 27 is in the position shown in FIG. 4, the filter designated by the numeral 7 in FIG. 4 is in the field of view of the camera 20. By way of example, this filter may be a readily commercially available filter for a green fluorescent dye. Turning to FIG. 8, it can be seen that by energizing motor 44 to controllably rotate screw 46, the filter array can be moved along the X-coordinates of plane "P" from the position shown in FIG. 4 to the position shown in FIG. 8 wherein the filter designated by the numeral 9 is disposed within the field of view of the camera 20. By way of example, filter 9 may be a readily commercially available filter for a red fluorescent dye. Turning to FIG. 9, it can be seen that by energizing motor 36 to rotate screw 38, the filter array can be moved along the Y-coordinates of plane "P" from the position shown in FIG. 8 to the position shown in FIG. 9 wherein the filter designated by the numeral 3 is disposed within the field of view of the camera 20. By way of example, filter 3 may be a readily commercially available filter for an orange fluorescent dye. The remaining filters in the array can be selected to filter various colors of fluorescent dyes, such as yellow, blue, indigo, violet, gold and for non-visible infrared and ultraviolet.

It is apparent that by selectively energizing motors 36 and 44, either manually or by a specially designed software, filter assembly 27 can be moved along the X and Y coordinates of plane "P" in a manner to precisely move any one of the filters of the nine filter array filter assembly 27 into the field of view of camera 20. Advantageously, by having nine filters in the filter array, the operator can quickly and easily move into the field of view of the camera the appropriate filter for filtering the particular fluorescent dye used in the specimen being analyzed. Additionally, if desired the filter grid can easily be removed and replaced with another filter grid embodying a plurality of differently configured filters.

Having now described the invention in detail, in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An imaging system for obtaining images of a specimen comprising:
   (a) a support for supporting the specimen;
   (b) a camera having a field of view, said camera being positioned relative to said support, so that said specimen is within said field of view of said camera;
   (c) filter means disposed proximate said support for filtering energy emitted from said specimen, said filter means comprising a filter array for supporting a plurality of emission filters in a side-by-side relationship, said filter array being disposed within a plane having X and Y coordinates; and
   (d) positioning means for positioning said filter array relative to said field of view of said camera, said positioning means comprising guide means operably associated with said filter array for guiding travel of said filter array along said X and Y coordinates of said plane to position a selected one of said plurality of emission filters within the field of view of said camera, said guide means comprising a filter array guide means for guiding travel of said filter array along said X-axis of said plane, said filter array guide means comprising pair of spaced apart first guide rods connected to said filter array each said pair of spaced apart first guide rods including a first extremity and second extremity, said filter array being slidably moveable along side first guide rods, said filter array and said pair of spaced apart first guide rods cooperating to comprise a filter array assembly, said filter array assembly further comprising a pair of support bearings connected to said first extremities of said pair of spaced apart first guide rods and a pair of support bearings connected to second extremities of said spaced apart second guide rods.

2. The imaging system as defined in claim 1 in which said guide means comprises a filter array assembly guide means for guiding travel of said filter array assembly along said Y-axis of said plane, said filter array assembly guide means comprising a pair of spaced apart second guide rods connected to said filter array assembly, said filter array assembly being slidably movable along said second guide rods.

3. The imaging system as defined in claim 2 in which a pair of said support bearings are slidably carried by one of said guide rods of said second pair of guide rods and in which a pair of said support bearings are slidably carried by the other of said guide rods of said second pair of guide rods.

4. The imaging system as defined claim 3, in which said positioning means further includes filter array assembly drive means for moving said filter array assembly along said second pair of guide rods.

5. The imaging system as defined in claim 4 in which said filter array assembly drive means comprises:
   (a) a threaded screw operably interconnected with said filter array assembly; and
   (b) an electric motor connected to said threaded screw for imparting rotation thereto.

6. An imaging system for obtaining images of a specimen comprising:
   (a) a support for supporting the specimen;
   (b) a camera having a field of view, said camera being positioned relative to said support, so that the specimen is within said field of view of said camera; and
   (c) filter means superimposed over said support for filtering energy emitted from said specimen, said filter means comprising a filter array for supporting a plurality of emission filters in a side-by-side relationship, said filter array being disposed within a plane having X and Y coordinates; and
   (d) positioning means for positioning said filter array relative to said field of view of said camera, said positioning means comprising guide means operably associated with said filter array for guiding travel of said filter array along said X and Y coordinates of said plane to position a selected one of said plurality of emission filters within the field of view of said camera, said guide means comprising:
      (i) a filter array guide means for guiding travel of said filter array along said X coordinates of said plane, said filter array guide means comprising pair of spaced apart first guide rods connected to said filter array, said filter array being slidably movable along said first guide rods, said filter array and said pair of spaced apart first guide rods cooperating to comprise a filter array assembly; and
      (ii) a filter array assembly guide means for guiding travel of said filter array assembly along said Y coordinates of said plane, said second guide means comprising a pair of spaced apart second guide rods connected to said filter array assembly, said filter array assembly being slidably movable along said second guide rods.

7. The imaging system as defined in claim 6 in which said filter array comprises nine generally rectangular shaped emission filters.

8. The imaging system as defined in claim 6 in which each of said pair of spaced apart first guide rods includes a first extremity and a second extremity and in which said filter array assembly further comprises a pair of support bearings connected to said first extremities of said pair of spaced apart first guide rods and a pair of support bearings connected to said second extremities of said spaced apart second guide rods.

9. The imaging system as defined in claim 6, in which said positioning means further includes filter array drive means for moving said filter array along said first pair of guide rods.

10. The imaging system as defined in claim 6, in which said positioning means further includes filter array assembly drive means for moving said filter array assembly along said second pair of guide rods.

11. The imaging system as defined in claim 10 in which said filter array drive means comprises:
 (a) a threaded screw operably interconnected with said filter array; and
 (b) an electric motor connected to said threaded screw for imparting rotation thereto.

12. An imaging system for obtaining images of a specimen comprising:
 (a) a support for supporting the specimen;
 (b) a camera superimposed over said support, said camera having a field of view; and
 (c) filter means superimposed over said support for filtering energy emitted from said specimen, said filter means comprising a filter array for supporting a plurality of emission filters in a side-by-side relationship, said filter array being disposed within a plane having X and Y coordinates and comprising nine generally rectangular-shaped emission filters;
 (d) positioning means for positioning said filter array relative to said field of view of said camera;
 (e) guide means operably associated with said filter array for guiding travel of said filter array along said X and Y coordinates of said plane to position a selected one of said nine generally rectangular-shaped emission filters within the field of view of said camera, said guide means comprising:
  (i) a filter array guide means for guiding travel of said filter array along said X coordinates of said plane, said filter array guide means comprising a pair of spaced apart first guide rods connected to said filter array, said filter array being slidably movable along said first guide rods, said filter array and said pair of spaced apart first guide rods cooperating to comprise a filter array assembly; and
  (ii) a filter array assembly guide means for guiding travel of said filter array assembly along said Y coordinates of said plane, said filter array assembly guide means comprising a pair of spaced apart second guide rods connected to said filter array assembly, said filter array assembly being slidably movable along said second guide rods:
   a. filter array drive means for moving said filter array along said first pair of guide rods; and
   b. filter array assembly drive means for moving said filter array assembly along said second pair of guide rods.

13. The imaging system as defined in claim 12 in which each of said pair of spaced apart first guide rods includes a first extremity and a second extremity and in which said filter array assembly further comprises a pair of support bearings connected to said first extremities of said pair of spaced apart first guide rods and a pair of support bearings connected to said second extremities of said spaced apart second guide rods.

14. The imaging system as defined in claim 12 in which said filter array drive means comprises:
 (a) a threaded screw operably interconnected with said filter array; and
 (b) an electric motor connected to said threaded screw for imparting rotation thereto.

15. The imaging system as defined in claim 12 in which said filter array assembly drive means comprises:
 (a) a threaded screw operably interconnected with said filter array assembly; and
 (b) an electric motor connected to said threaded screw for imparting rotation thereto.

* * * * *